United States Patent [19]
Warwick et al.

[11] Patent Number: 6,042,543
[45] Date of Patent: Mar. 28, 2000

[54] TEST DEVICE AND METHOD FOR QUANTITATIVE MEASUREMENT OF AN ANALYTE IN A LIQUID

[75] Inventors: Warren J. Warwick, Minneapolis; Leland G. Hansen, St. Paul, both of Minn.

[73] Assignee: Regents of the University of Minnesota, Minneapolis, Minn.

[21] Appl. No.: 08/950,523

[22] Filed: Oct. 14, 1997

Related U.S. Application Data

[60] Provisional application No. 60/040,665, Mar. 11, 1997.

[51] Int. Cl.$^7$ .................................................... A61B 5/00
[52] U.S. Cl. .................... 600/362; 600/346; 600/309; 600/367; 422/56; 422/58; 436/165
[58] Field of Search .................... 600/362, 346, 600/348, 367, 309, 345, 347, 361, 365; 422/56, 58; 436/165

[56] References Cited

U.S. PATENT DOCUMENTS

| | | | |
|---|---|---|---|
| 3,552,929 | 1/1971 | Fields et al. | 23/253 |
| 4,444,193 | 4/1984 | Fogt et al. | 128/632 |
| 4,457,748 | 7/1984 | Lattin et al. | 604/20 |
| 4,650,768 | 3/1987 | Cahill et al. | 436/125 |
| 4,846,182 | 7/1989 | Fogt et al. | 128/632 |
| 5,050,604 | 9/1991 | Reshef et al. | 600/309 |
| 5,131,390 | 7/1992 | Sakaguchi et al. | 600/309 |
| 5,741,330 | 4/1998 | Brauker et al. | 623/11 |

OTHER PUBLICATIONS

Coury et al., "Development of a Screening System for Cystic Fibrosis," *Clin. Chem.*, 29(9), 1593–1597 (1983).
*CF Indicator*™ *Sweet Test System*, a Brochure by Medtronic, Inc., Table of Contents, pp. 1–31 (not dated).
Gibson et al., "A Test for Concentration of Electrolytes in Sweat in Cystic Fibrosis of the Pancreas Utilizing Pilocarpine by Iontophoresis," *Pediatrics*, 23, 545–549 (Mar. 1959).
Kollberg et al., "A new Reliable Sweat Test," in *Cystic Fibrosis: Horizons, Proceedings of the 9$^{th}$ International Cystic Fibrosis Congress*, Brighton, England, Jun. 9$^{th}$–15$^{th}$, 1984, p. 205.
Warwick et al., "Comparison of the error due to the use of gauze and filter paper in the gravimetric chloride titration sweat test," *Am. J. Clin. Pathol.*, 72(1), 211–215 (Jul. 1979).
Warwick et al., "Comparison of the Chloride Electrode and Gravimetric Chloride Titration Sweat Test," *Am. J. Clin. Pathol.*, 72(1) 142–145 (Jul. 1979).
Warwick et al., "Sweat Testing of Infants and Young Children Using a 30 Microliter Paper Patch," in *Cystic Fibrosis: Horizons, Proceedings of the 9$^{th}$ International Cystic Fibrosis Congress*, Brighton, England, Jun. 9$^{th}$–15$^{th}$, 1984, p. 206.
Warwick et al., "Evaluation of Cystic Fibrosis Screening System Incorporating a Miniature Sweat Simulator and Disposable Chloride Sensor," *Clin. Chem.*, 32(5), 850–853 (1986).
Warwick et al., "Quantification of Chloride in Sweat with the Cystic Fibrosis Indicator System," *Clin. Chem.*, 36(1), 96–98 (1990).
Yeung et al., "Evaluation of a Paper patch Test for Sweat Chloride Determination," *Clinical Pediatrics*, 23(11), 603–607 (Nov. 1984).

*Primary Examiner*—Max Hindenburg
*Assistant Examiner*—Navin Natnithithadha
*Attorney, Agent, or Firm*—Haugen Law Firm PLLP

[57] ABSTRACT

A device and method for determining the concentration of an analyte, particularly a chloride ion, in a liquid sample are particularly useful to screen for cystic fibrosis in an individual. In a preferred embodiment, the device takes the form of a patch comprising an absorbent material sandwiched between two liquid-impermeable layers. Chloride ions in the liquid sample complex with a chloride-detecting agent dispersed throughout the absorbent material to form a visible precipitate, preferably silver chloride. A pH indicator is also dispersed throughout the absorbent material, allowing the position of the water front to be monitored thereby permitting calculation of chloride concentration from a partially filled patch.

35 Claims, 3 Drawing Sheets

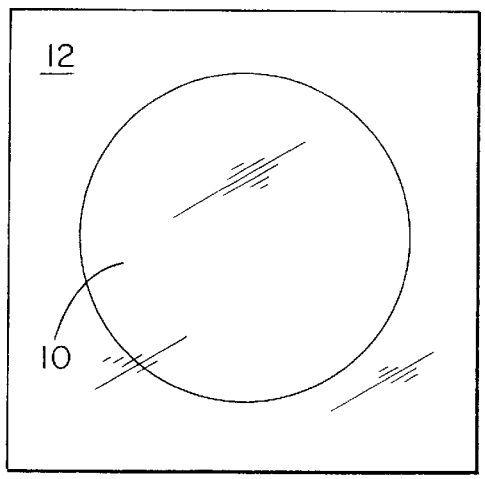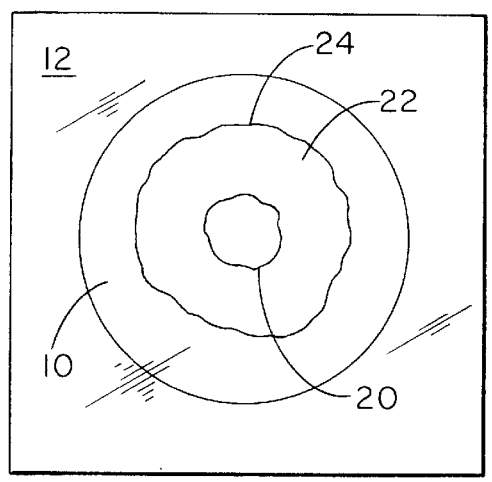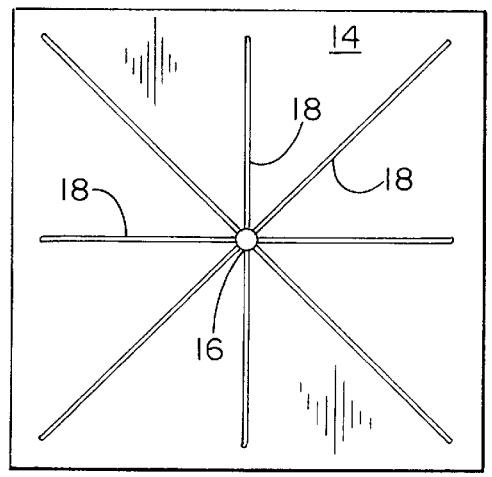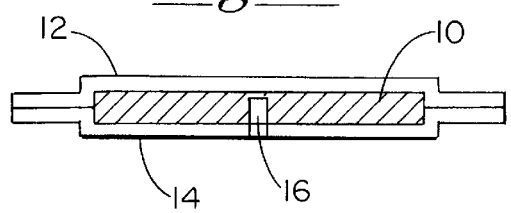

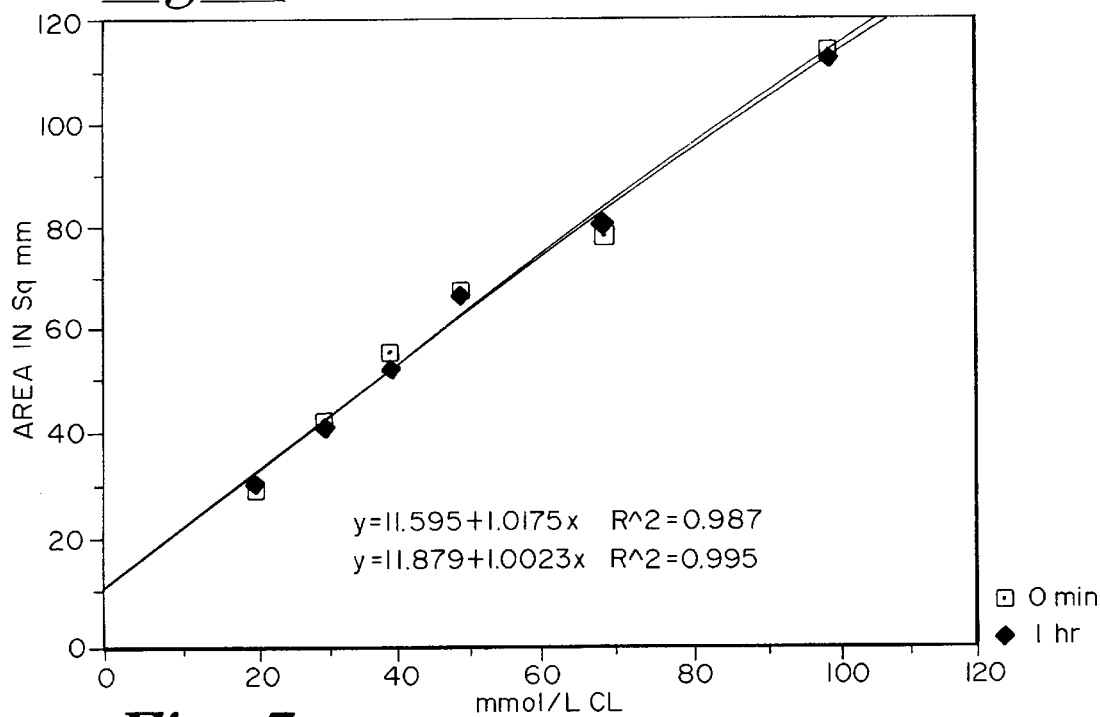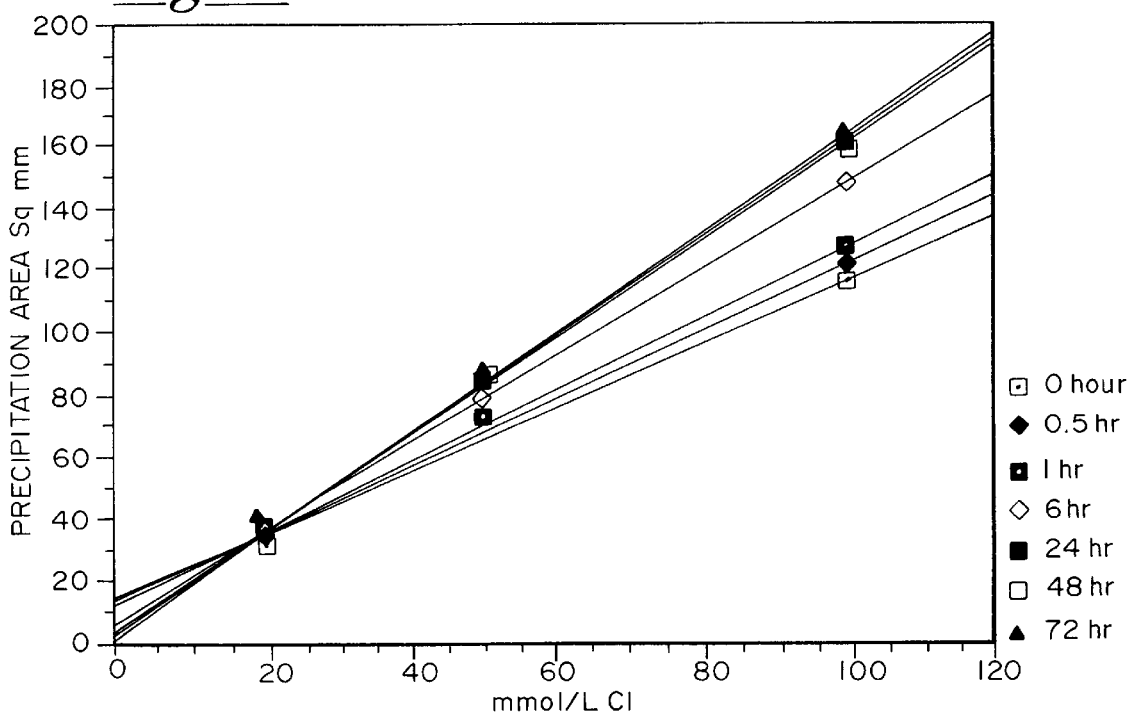

6,042,543

TEST DEVICE AND METHOD FOR QUANTITATIVE MEASUREMENT OF AN ANALYTE IN A LIQUID

This application claims the benefit of U.S. Provisional application Ser. No. 60/040,665, filed Mar. 11, 1997, which is incorporated herein in its entirety.

BACKGROUND OF THE INVENTION

At an incidence of 0.5 to 1.0 per 1000 births, cystic fibrosis (CF) is one of the most common fatal genetic disorders. Fortunately, its debilitating complications are sometimes avoided by early application of prophylactic and therapeutic measures, making early detection of CF important.

There is a close correlation between excessive concentrations of chloride ($Cl^-$) and sodium ($Na^+$) in sweat and the presence of the clinical syndrome. Typically, sweat chloride values in CF patients exceed 60 mmol/L, whereas non-CF subjects ordinarily have sweat chloride values of less than 40 mmol/L.

The "sweat test" is considered the definitive laboratory test for the diagnosis of CF. The three steps involved in all sweat testing are stimulation of sweating, collection of sweat, and measurement of its salt content. The Gibson-Cooke sweat test (GCST), which provides a quantitative measure of chloride concentration in sweat, has been approved by the Cystic Fibrosis Foundation as the most definitive sweat test. However, it requires specifically prescribed procedures for each step, a high level of quality control, dedicated technicians, and frequent performance to maintain high diagnostic efficiency. Another CF detection system utilizes a disposable chloride-sensor patch to screen for CF, permitting a qualitative diagnosis of "normal", "possible CF", or "classic CF" by comparing sample concentrations of chloride with a predetermined chloride concentration level (Lattin et al., U.S. Pat. No. 4,457,748, issued Jul. 3, 1984; Fogt et al., U.S. Pat. No. 4,846,182, issued Jul. 11, 1989; Fogt et al., U.S. Pat. No. 4,444,193, issued Apr. 24, 1984; W. Yeung, M.D., et al., Clin. Pediatrics, 23, 603–607 (1984); W. Varwick et al., Clin. Chem. 32, 850–853 (1986)). The indicator patch must be carefully monitored so that it is neither underfilled or overfilled. Digitized measurement of the precipitation area in a filled 20-mg patch has been used to derive a mathematical relationship between the area of chloride precipitation and the chloride concentration of standard NaCl solutions (W. Warwick et al., Clin. Chem., 36, 96–98 (1990)).

Sweat test CF indicator systems that are simple to use but that yield quantitative determinations of chloride concentrations are thus desirable. A test device that is capable of generating accurate chloride determinations from small sample sizes is particularly desirable because of the difficulty of obtaining large sweat samples from very young subjects.

SUMMARY OF THE INVENTION

The present invention provides a quantitative test device for determining the concentration of an analyte in a liquid sample. The device includes a substantially flat absorbent material sandwiched between a first liquid-impermeable layer and a second liquid-impermeable layer which has an inlet for the introduction of the liquid sample. The material from which each of these two outer layers is fabricated may be the same or different. Preferably at least one of the liquid-impermeable layers is transparent to allow visualization of a flat surface of the absorbent material.

The absorbent material contains a partitioning agent capable of detectably removing the analyte from the liquid. Preferably, the partitioning agent is distributed in a substantially uniform manner throughout at least a portion of the absorbent material, which portion is in contact with the inlet. In one embodiment, a partitioning agent capable of binding the analyte, either covalently or noncovalently, to form a detectable bound complex, is bound to, sequestered, or otherwise immobilized on or within the absorbent material. For example, the partitioning agent can include a bound, sequestered, or otherwise immobilized biomolecule such as a protein, nucleic acid, or carbohydrate. Examples of partitioning agents include antibodies, antigens, enyzmes, lectins, hormones, and various other organic and inorganic ligands, such as biotin and avidin. The partitioning agent can also include bound, sequestered, or otherwise immobilized organic and inorganic ions, chelating agents, and the like. In an alternate embodiment, the partitioning agent is dispersed within the absorbent material includes a species, preferably an ionic species, capable removing the analyte from the liquid by way of in situ formation of a detectable complex comprising the analyte. Preferably, the detectable complex takes the form of an insoluble precipitate, deposit, gel, matrix, or the like, such as an insoluble salt.

In a particularly preferred embodiment, the sample analyte to be quantified is a chloride ion. A silver salt, preferably silver chromate or silver dichromate, which complexes with chloride ions in a liquid sample to form a silver chloride precipitate, is uniformly dispersed throughout the absorbent material.

The absorbent material additionally contains an agent capable of detectably delimiting the water front formed as the liquid sample diffuses through the absorbent material. This liquid-detecting agent is distributed throughout at least a portion of the absorbent material, preferably although not necessarily in a substantially uniform manner. Preferably the liquid-detecting agent is a pH indicator, such as phenol red. Detectability of the water front allows analyte concentrations to be calculated from partially filled test devices, obviating the need for careful monitoring of the device as the liquid sample diffuses through the absorbent layer so as to ascertain test completion. When a pH indicator is used to monitor the water front, the inlet in the bottom layer optionally includes a material capable of ensuring the pH of the sweat or other test sample is slightly basic, preferably at least about pH 7.0. A particularly suitable material is sodium bicarbonate ($NaHCO_3$) in the form of a paste. The presence of this alkaline substance ensures that there is a visible color change in the test device that marks the water front as the sweat or other test sample diffuses into the absorbent layer from the inlet.

In a preferred embodiment for use in diagnostic testing, the collection and testing device includes a sheet of absorbent material sandwiched between top and bottom layers of transparent nonpermeable material. A centrally located inlet opening, preferably a small hole, extends through the bottom layer and preferably into the layer of absorbent material. The bottom layer of the device contains a fluid collector, such as a set of radial channels, which directs the sample to the inlet opening. The diagnostic test device is disposable and is fabricated for one-time use.

The invention also includes a method for making the present device. A preferred method includes loading the absorbent material by distributing throughout at least a portion thereof each of (i) a liquid-detecting agent that permits detection of the water front as the sample migrates from the inlet through the absorbent material and (ii) a partitioning agent capable of detectably removing the analyte from the liquid sample. After loading, the absorbent material is positioned between a first liquid-impermeable layer and a second liquid-impermeable layer that includes an inlet for introduction of the liquid sample.

The invention further includes a method for determining the concentration of an analyte in a liquid sample. An amount of the liquid sample is introduced into the inlet of the device such that the liquid diffuses through the absorbent material so as to contact both the liquid-detecting agent and the partitioning agent. Contact of the liquid with the liquid-detecting agent allows detection of the water front, which delimits a region within the absorbent material referred to herein as the "fill area." Contact of the liquid with the partitioning agent causes formation of a detectable complex that includes the analyte, thereby effecting removal of the analyte from the liquid. The detectable complex may include a bound, sequestered, or immobilized complex, or a precipitate, deposit, gel, matrix, or the like, and the region of its formation is referred to herein as the "detection area" of the absorbent material.

The boundaries or areas of the detection area and fill area are detectable in order to permit measurement of their respective areas. The suitability of various detection methods is influenced by the nature of the liquid-detecting agent used and detectable analyte-containing complex formed. Useful detection methods include, for example, spectroscopic methods to detect absorbence or emission of ultraviolet, visible, or infrared light, radiometric or radiographic methods, enzymatic methods, and the like. Preferably, the detection and fill areas are visually detectable by way of an observable difference in color.

Two-dimensional area measurements of the detection area and fill area are made, preferably using a computer, and the measurements are used to determine the concentration of the analyte in the liquid sample. Where the liquid-detecting agent and the partitioning agent are each uniformly distributed throughout the entire test area of the test device, and where the inlet is in the form of a small hole, a liquid sample containing an analyte that is introduced into the inlet of the test device will diffuse through the absorbent material causing formation of a fill area and a detection area each substantially concentric around the small hole, facilitating measurement of the areas. Concentration of the analyte in the liquid sample is calculated from the area measurements using a standard curve or mathematical equation associated with the test device.

An alternate embodiment of the device of the invention thus includes a first liquid-impermeable layer, a second liquid-impermeable layer comprising an inlet for the introduction of the liquid sample, and a third layer between the first and second liquid-impermeable layers comprising an absorbent material that includes (i) a measurable fill area delimited by the detectable water front formed as a liquid sample diffuses through the device after introduction at the inlet, and (ii) a measurable detection area formed as a result of the immobilization, fixation, precipitation, or the like, of a detectable complex comprising the analyte of interest originally present in the liquid sample.

When used as a diagnostic test for cystic fibrosis, the method of the invention further includes inducing the production of sweat on the skin of a patient and applying the bottom layer of the device to the skin of the patient such that the sweat enters the device through the inlet and diffuses through a portion of the absorbent material to yield a precipitation area comprising a detectable precipitate comprising the chloride ions, and a fill area detectably delimited by the liquid front. The concentration of chloride in the sweat, determined by evaluating the precipitation and fill areas, is indicative of the presence or absence of cystic fibrosis in the subject.

The invention further includes a diagnostic kit for screening for cystic fibrosis. The kit includes at least one test device, instructions for use, and, optionally, a known amount of a chloride salt or a solution containing a known concentration of chloride ions, and at least one test device to serve as a quality control. Preferably, the chloride ions are provided as sodium or potassium chloride.

The present device employs a much simpler construction than the device disclosed in U.S. Pat. No. 4,444,193. In contrast to the multiple heterogenous internal layers and different absorbent zones of the indicator device of U.S. Pat No. 4,444,193 (see, e.g., FIG. 3 therein), the present device preferably utilizes a single layer of absorbent material that is easily pretreated to distribute a water front indicator and a partitioning agent throughout at least a portion of the absorbent layer prior to sealing between the two impermeable outer layers. Moreover, the present device is a more reliable diagnostic tool in a clinical setting because the device is designed to be removed from the sample source after only partial filling, as evidenced by a still-detectable water front. The extent of partial filling, above a certain minimum, is not critical because the detection area and fill area measurements can be extrapolated to a "complete fill" by using the standard curve and the associated regression equation. Overfilling of the present device is thus easily detected: the water front is no longer visible. In that event, the diagnostic test is preferably repeated. In contrast, the device of U.S. Pat. No. 4,444,193 must be completely filled, but not overfilled, to provide accurate results. To that end, the device of U.S. Pat. No. 4,444,193 contains a tab portion designed to visually signal a complete fill of the patch. Careful monitoring of the prior art device is required, and overfilling is difficult to detect unless the tab portion of the patch is actually being observed as complete fill is approached.

BRIEF DESCRIPTION OF THE DRAWINGS

FIG. 1 shows (a) a top view of a collection and testing device according to the invention prior to use and (b) a top view of the collection and testing device after introduction of a liquid sample containing an analyte.

FIG. 2 is a bottom view of a collection and testing device according to the invention.

FIG. 3 is a schematic cross section taken through the center of a collection and testing device according to the invention.

FIG. 4 is a graph depicting regression lines fit to a plot of extrapolated precipitation area versus chloride concentration at 0 minutes (squares) and 1 hour (diamonds) after removal of the partially filled patches from the sample source. The precipitation area was measured using a computer digitizer.

FIG. 5 is a graph depicting regression lines fit to a plot of precipitation area versus chloride concentration for completely filled patches (about 20 mg sample) at times from ranging from zero to 72 hours after removal of the filled test patches from the sample source (dotted squares, 0 hour; filled diamonds, 0.5 hour; dotted filled squares, 1 hour; open diamonds, 6 hours; filled squares, 24 hours; open squares, 48 hours; and triangles, 72 hours).

DETAILED DESCRIPTION OF THE PREFERRED EMBODIMENTS

Figure 6:
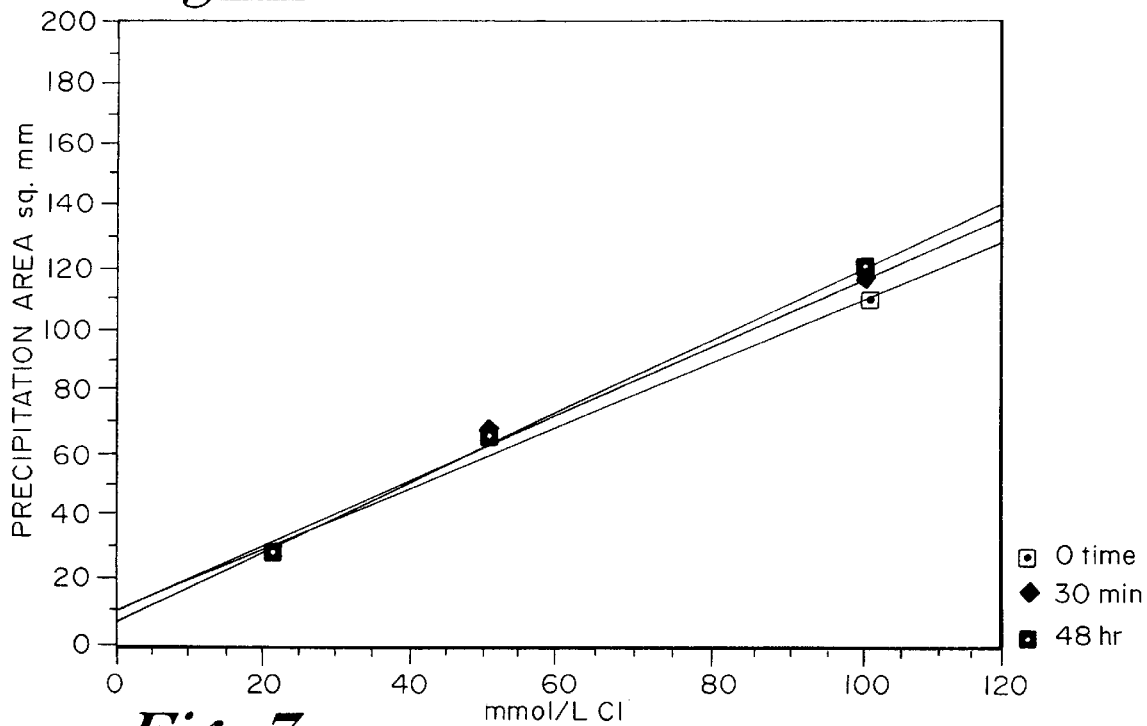
FIG. 6 is a graph depicting regression lines fit to a plot of precipitation area versus chloride concentration for completely filled patches (about 20 mg sample) at various times after removal of the filled test patches from the sample source (dotted squares, 0 hour; filled diamonds, 30 minutes; dotted filled squares, 48 hours). The filled test patches were dried over $CaSO_4$.

A preferred embodiment of the device allows for a quantitative determination of chloride concentration in a liquid sample, particularly sweat. A particularly preferred embodiment of the device is intended for use in diagnosis of cystic fibrosis. It is to be understood that the device, nonetheless, is generally useful for determining the concentration of a dissolved analyte in any liquid sample. Advantageously, the device is constructed and arranged to accommodate variable sample sizes.

FIGS. 1 and 2 show the top and bottom surfaces, respectively, of a sweat collection and testing device of the invention. A cross-sectional side view is shown in FIG. 3. In the preferred embodiment, the device takes the form of a patch that includes a single layer of substantially flat absorbent material 10 having a substantially uniform thickness, sandwiched between two outer layers (i.e., a top layer 12 and a bottom layer 14, together forming an "envelope" enclosing the absorbent material). The absorbent material 10 comprises the "test area" of the patch. The terms "substantially flat" and "substantially uniform thickness" are used herein to describe a sheet-like absorbent material having about the same surface area to cross-sectional volume ratio throughout at least the "test area" of the patch. Since the device is designed to receive a fluid sample that only partially fills the absorbent layer 10, the device need not, but optionally can, include a "complete fill" indicator, such as a tab, a concentric outer region, or other element (see, e.g., the device of U.S. Pat. No. 4,444,193, col. 2, lines 59–65).

The preferred absorbent material is filter paper or chromatography paper, for example Chromatography Paper No. 20 (Whatman, Inc., Clifton., N.J.). The volume of sample that can be absorbed by the device is variable and depends on the size and weight of the absorbent paper selected. The shape of the test area is not limited in the invention, however the use of a circular area formed by an absorbent paper disk is convenient for visualization of concentric detection and fill areas in the preferred embodiment.

The outer layers are fabricated from a material that is impermeable to liquids. The nonpermeable material in each of the two outer layers may be the same or different. Preferably, the nonpermeable material of the top layer is transparent. In a preferred embodiment, the total patch area is larger than the test area, and the outer layers encase the test area and contact each other around its perimeter (see FIG. 1 and FIG. 3). A waterproof sealant that does not interfere with measurement of the concentration of the sample analyte is used to secure the layers. A polyester tape, such as Lab Label Protection Tape (Bel-Art Products, Pequannock, N.J.), is transparent and contains its own sealant in the form of a tacky surface, and thus is an especially suitable nonpermeable material.

As shown in FIG. 2 and FIG. 3, a small inlet hole 16, for sample introduction, extends through the bottom layer 14 and preferably into the layer of absorbent material 10. It is desirable, although not necessary, that the small hole 16 be centrally located in the bottom layer 14, and centrally located in the absorbent material 10. Typically the diameter of the hole is greater than about 0.05 mm and less than about 2 mm. Preferably, the diameter of the hole is about 0.5 mm to about 1.5 mm. Optionally, the small hole can contain a wick to aid in delivery of the liquid sample to the absorbent layer. The bottom layer 14 preferably also contains grooves or channels 18 to direct sweat toward the inlet hole 16.

The shape of the patch is not limited in the invention, but typically the patch is fabricated as a rectangle or circle. The total patch area is generally less than about 25 $cm^2$, preferably less than about 20 $cm^2$. The total patch area is preferably greater than about 5 $cm^2$, more preferably greater than about 10 $cm^2$. The test area of the patch is typically less than about 10 $cm^2$, more preferably less than about 5 $cm^2$. Preferably, the test area is greater than about 1 $cm^2$, more preferably greater than about 2 $cm^2$.

The absorbent material is impregnated with a partitioning agent preferably comprising a soluble silver salt, such as silver chromate ($AgCrO_4$) or silver dichromate ($Ag_2Cr_2O_7$). The soluble silver salt is dispersed substantially uniformly throughout at least a portion the absorbent material, preferably throughout a portion that includes or is in direct contact with the inlet, more preferably throughout the entire test area of the absorbent material. When a sweat sample contacts the soluble silver salt, a white insoluble silver chloride precipitate is formed, thereby removing the chloride ions from solution. The area of formation of this precipitate, i.e., the "detection area" or, in this case, "precipitation area," expands as the liquid disperses throughout the absorbent material. FIG. 1(b) shows a detection area 20 formed during introduction of a liquid sample.

In the preferred embodiment the absorbent material is also impregnated with a liquid-detecting agent comprising a pH indicator, preferably phenol red, to detect the location of the water front as a liquid sample diffuses through the absorbent material. The liquid-detecting agent is dispersed throughout at least a portion of absorbent material, preferably throughout at least an annular portion about the inlet, more preferably throughout the entire test area of the absorbent material. FIG. 1(b) shows a fill area 22 delimited by the water front 24 at a point during the introduction of a liquid sample. During sample collection, the water front moves, and the fill area expands, as the device takes on an increasing amounts of liquid sample.

The test area of the absorbent material comprises the region of substantially uniformly dispersed partitioning agent and the region of dispersed liquid-detecting agent. These regions preferably are, but need not be, the same. The test area thus comprises the "fill area" and "detection area" which form during and are present after contact of the device with a liquid sample. The upper limit of the detection area is the fill area, since the analyte cannot migrate ahead of the water front.

The pH indicator used in the preferred embodiment of the test device, phenol red, produces a visible color change at about pH 7.0. Other pH indicators that are suitable for use in the test device include bromocresol green, bromothymol blue, and methyl red, although they are not as desirable as phenol red. pH indicators that do not contain halogens are generally preferred because their use eliminates the possibility that the halogen will interfere with the precipitation reaction, particularly if the precipitate is AgCl.

The inlet of the device optionally includes a material capable of ensuring that the pH of the sweat or other test sample is slightly basic, preferably at least about pH 7.0, as it diffuses through the absorbent material. A preferred material is sodium bicarbonate (NaHCO$_3$) in the form of a paste or a plug. A suitable paste can be prepared by adding distilled water to 1 gram of sodium bicarbonate until a paste is formed. This presence of this paste or plug at the small hole, where the sample enters the device, ensures that there is a visible color change marking the water front as the sweat or other test sample diffuses radially away from the hole into the absorbent layer of the test device.

When the device is placed on the skin, sweat being secreted on the skin is taken up through the small hole into the absorbent material. As liquid migrates out from the center hole into the absorbent material, chloride ions present in the liquid react with silver ions of the impregnated silver salt to form silver chloride (AgCl). The silver chloride forms a stable precipitate which is typically lighter in color than the unreacted silver salt. The area of the precipitate can be measured and is proportional to the number of chloride ions present in the sample.

The liquid portion of the sweat sample causes an observable color change in the test device as it contacts the pH indicator, e.g., phenol red, dispersed throughout the absorbent material. The fill area thereby delimited by the water front is measurable and proportional to the sample size. Quantitative calculations of chloride concentration in a liquid sample can be made using measurements of the precipitation area and the fill area. The present device permits calculation of chloride concentration in relatively small samples, often as low as 5 mg, when the device is only partially filled. This is particularly advantageous for screening newborns who often produce too little sweat for conventional devices.

A preferred embodiment of the method of the invention involves contacting the test device with a liquid sample such that the sample enters the device through the small hole and diffuses radially outward from the hole through the absorbent layer. The test device is applied to the skin of a human subject after the skin has been stimulated to produce sweat. Electrical stimulation using an iontophoretic generator (a sweat stimulator) to deliver pilocarpine to the human subject is a commonly used method (e.g., W. Warwick et al., *Clin. Chem.*, 32, 850–853 (1986)). The skin area is then cleaned with distilled water and dried, and the test device is taped over this cleaned area with the collector side of the device next to the skin. As sweat is generated, the collector channels direct it toward the inlet opening where it enters the device by passing through the basic plug. The sweat diffuses radially out from the inlet opening, and chloride ions in the sweat combine with the silver ions of the silver chromate and to form a precipitate. The water front is visualized by a color change effected by the pH indicator. After a sufficient amount of sample has been absorbed, the test device is removed from the sample source (e.g., the skin of the human subject), and the chloride concentration of the sample is calculated based upon an empirically derived linear relationship between AgCl precipitation area and chloride concentration calculated from a set of chloride standards having various concentrations. Substantially uniform dispersal of the partitioning agent (in this case, silver chromate) throughout the substantially flat absorbent material of substantially uniform thickness allows for a two-dimensional measurement of the detection area that is proportional to the amount of the analyte-containing detectable complex formed in the associated cross-sectional volume, rendering the size of the detection area proportional to the concentration of the analyte in the liquid sample.

In the case of a partially filled patch, the measured detection area can be converted to an extrapolated detection area (i.e., the detection area that would have been observed if the patch had been completely filled with the sample) by multiplying the measured detection area by the ratio of total test patch area (for a complete fill) to actual filled area (in the partially filled patch). The extrapolated detection area was found vary linearly with chloride concentration in the sample. Likewise, the ratio of the measured detection area to measured fill area in a partially filled patch also varies linearly with the concentration of chloride in the liquid sample. The chloride ion concentration in a test sample can therefore be conveniently determined by reference to a graph showing either (i) the extrapolated detection area or (ii) the ratio of measured detection area to measured fill area, as a function of chloride concentration. The mathematical relationship between the measured variable and chloride concentration (referred to generally as a "standard curve") is empirically derived (via linear regression) from a set of chloride standards having various concentrations. Preferably, the sample size is at least about 3 mg, more preferably at least about 5 mg. A 5 mg sample typically yields a fill area about 1 cm in diameter.

The linear regression equation that describes the relationship between the measured variable and the chloride (or other analyte) concentration in a sample is conveniently derived by analyzing a series of liquid samples each containing a known, different concentration of chloride ion. For example, each sample can be introduced into a device such that each device is partially filled. The sample volume present in each device can be determined by weighing the device before and after introduction of the sample. The observed precipitation areas and fill areas are then measured, and the ratios are plotted against the known chloride concentration of the samples. Alternatively, the measured detection area can be extrapolated to an extrapolated detection area, as described above, and the extrapolated detection area can be plotted against the known chloride concentrations. Linear regression is performed, and the resulting standard curve can be used to calculate the chloride concentration from measurements made on a partially filled device containing a test sample having an unknown concentration of chloride ions.

Detection areas and fill areas can be measured using any convenient means. Preferably, the areas are digitized using a computer scanner. The patch or an image thereof (such as a photocopy or photograph) can be scanned into a computer, and the areas can be calculated from the scanned images. Preferably, a computer program or algorithm is used to calculate the number of pixels present in each area, and the area is calculated based upon the number of pixels. The computer can then directly calculate the analyte concentration based upon the mathematical information that characterizes the relationship between detection area (or extrapolated detection area) and analyte concentration. In a preferred embodiment, patient identification data is also input into the computer, and the computer automatically associates the test results with the appropriate patient data.

These areas can also be measured with a computer digitizer using a stylus pen and an array detector. Visible detection and fill areas can also be manually measured using a caliper or similar instrument. A grid may be placed over the test device for use in estimating areas, or one of the nonpermeable, transparent layers can contain grid markings to aid in area determination.

In a preferred embodiment of the method of making the present device, silver chromate (or silver dichromate) and a pH indicator are each substantially uniformly dispersed throughout all or a substantial portion of the substantially flat absorbent layer prior to forming the patch. Impregnation of the absorbent layer with silver chromate is preferably accomplished by applying solutions of silver nitrate ($AgNO_3$) and potassium chromate ($K_2CrO_4$) to the absorbent layer. For example, the concentration of $AgNO_3$ in the silver nitrate solution is preferably greater than about 0.01M, more preferably greater than about 0.05M. The concentration of silver nitrate ($AgNO_3$) in the silver nitrate solution is preferably less than about 0.5M, more preferably less than about 0.3M, most preferably less than about 0.2M. The concentration of potassium chromate ($K_2CrO_4$) in the potassium chromate solution is preferably greater than about 0.005M, more preferably greater than about 0.01M. The concentration of potassium chromate ($K_2CrO_4$) in the potassium chromate solution is preferably less than about 0.5M, more preferably less than about 0.2M, most preferably less than about 0.1M. The silver chromate ($Ag_2CrO_4$) should be reproducibly and evenly distributed within the absorbent material. Typically the absorbent material, such as a sheet of chromatography paper, is first wetted with a silver nitrate solution, dried, then wetted with a potassium chromate solution to form the silver chromate in situ. The absorbent material, impregnated with silver chromate, is then wetted with a solution containing the desired pH indicator, preferably phenol red, and dried. An inert, waterproof sealant is applied to the surface of each of the two liquid-impermeable outer layers, and the absorbent material, impregnated with silver chromate and the pH indicator, is positioned between a top and a bottom outer impermeable layer so as to contact the surfaces of the outer layers comprising the sealant and be sandwiched between them, thus forming the patch. Preferably, the top and bottom layers are in direct contact with, and thus sealed to, each other around the perimeter of the substantially flat absorbent material. Conveniently, the outer layers can be formed from a tape comprising the waterproof sealant on one side. The top layer is transparent. The bottom layer is pierced, either before or after formation of the patch, to form the small inlet hole for introduction of a sample. Optionally the hole extends through the absorbent layer. In a particularly preferred embodiment, the bottom layer is scored to form channels to facilitate delivery of a liquid sample to the inlet hole of the device (see FIG. 2).

Because uniform dispersal of the pH indicator is not critical, an alternative method contemplates forming the layered patch after impregnating the absorbent material with the silver chromate but before applying the pH indicator. Formation of the patch is followed by delivery of a solution of the pH indicator to the inlet hole in the bottom layer such that the solution migrates throughout substantially all the absorbent material. After drying, the device is ready for use.

The diagnostic method of the invention is preferably used to detect cystic fibrosis in a patient. Typically, chloride concentration in human sweat is less than 40 mmol/L. In CF patients, however, the value is generally in excess of 60 mmol/L. The lower limit of chloride measurement of the test device of the invention is about 10 mmol/L. The test device is not intended to be limited by any upper limit of detection. Preferably, the test device permits measurement of sample chloride concentrations up to about 200 mmol/L, more preferably up to about 100 mmol/L. A chloride level above that observed in a normal patient population, preferably a chloride level above about 60 mmol/L, is indicative of cystic fibrosis in the patient.

The present invention also includes a kit containing at least one test device, preferably in the form of a disposable flat patch, and optionally at least one standard chloride solution, preferably about 20–80 mmol/L chloride, more preferably about 30–60 mmol/L chloride, for use as a control. The standard chloride solution supplied as part of the kit preferably contains a soluble chloride salt, such as sodium chloride or potassium chloride, and preferably has a pH of at least about 7, more preferably between about pH 7 and about pH 7.5. In place of the chloride solution, the kit can contain a predetermined amount of chloride salt that can be used to prepare standard chloride solutions. The kit also includes instructions for clinical or laboratory use, and, optionally, a statistical analysis or equation that allows the observed precipitation areas to be mathematically converted to chloride concentrations for the test samples. Preferably, each test kit includes a plurality of extra test patches of the same lot number to be used with the control solution. A control solution can be applied to a test patch to assess or confirm the validity of patient test results.

Advantages of the invention are illustrated by the following examples. However, the particular materials and amounts thereof recited in these examples, as well as other conditions and details, are to be interpreted to apply broadly in the art and should not be construed to unduly restrict or limit the invention in any way.

EXAMPLES

The commercially available "CF INDICATOR" patch (Scandipharm, Inc., Birmingham, Ala.) is designed and marketed as a qualitative screening test for cystic fibrosis (CF). Use of the patch in compliance with instructions supplied therewith for its intended use permits a qualitative diagnosis of normal ([$Cl^-$]$\leq$40 mmol/L), possible CF (40 mmol/L<[$Cl^-$]$\leq$60 mmol/L), or classic CF ([$Cl^-$]>60 mmol/L). The following studies were designed and conducted in an effort to develop a new patch that could be used for quantitative measurement of chloride concentration ([$Cl^-$]).

Example 1

Sample Chloride Concentration vs. Extrapolated Silver Chloride Precipitation Area for the Chloride Test Patch The following experiment was designed to determine whether chloride concentration ([$Cl^-$]) of a sample can be measured using a partially filled test device.

Materials. A test device was fabricated by Scandipharm, Inc., using methods substantially as disclosed for the "CF INDICATOR" Patch (U.S. Pat. No. 4,444,193, incorporated herein by reference in its entirety). A small disk (about 1.9 cm in diameter) of Chromatography Paper No. 20 (Whatman, Inc., Clifton N.J.) was wetted with a silver nitrate solution (0.1M $AgNO_3$), dried, then wetted with a potassium chromate solution (0.07M $K_2CrO_4$) to form a brown precipitate of silver chromate in situ, as described in U.S. Pat. No. 4,444,193. The absorbent disk, impregnated with silver chromate, was then sandwiched between two square pieces (each having an area of about 3.9 square centimeters ($cm^2$)) of transparent Lab Label Protection Tape (Bel-Art Products, Pequannock, N.J.). The bottom layer was pierced to form a 1 mm inlet hole. The test area was about 283 square millimeters ($mm^2$), and the total patch area was about 1444 $mm^2$ (14.44 $cm^2$). The resulting test device contained the same type, and about the same amount, of absorbent material as the commercially available "CF INDICATOR" Patch and thus, when completely filled, held the about same amount (about 20 mg) of liquid sample.

Most test patches used in this experiment contained a tab area that provided an indication of a fill "complete fill" (i.e., around 20 mg sample). However, the test patch did not have a "blanking region" that is present in a "CF INDICATOR" Patch (U.S. Pat. No. 4,444,193). Rather, the entire absorbent region of the patch, including the tab, was impregnated with $Ag_2CrO_4$. The actual concentration of silver chromate is not critical, but the silver chromate must be uniformly dispersed throughout the patch and essentially the same for each patch used in any given experiment. The silver chloride concentration must be consistent for any control patches used as standards to derive an associated standard curve or linear regression equation.

Methods. An aqueous (0.04%) solution of phenol red (LabChem, Inc) was introduced throughout the absorbent material of the patch by applying it to the central hole and letting it diffuse out radially. The patch was then dried down to within 2 percent of its original dry weight. In some experiments, a small paste pellet of $NaHCO_3$ was added to the fill hole of the patch after drying in order to maintain an alkaline pH for the diffusing sample when in use.

The resulting test patches containing the phenol red were exposed to aqueous test samples (Table 1) containing various known concentrations of NaCl. Collection was stopped after partially filling a test patch. Sample sizes were determined by subtracting the dry weight of the test patch from the wet weight of the patch after removal from the sample source, and ranged from 5.2 mg to 8.9 mg.

TABLE 1

Sample Weights for Partially Filled Patches

| Chloride Concentration | Sample Weight |
|---|---|
| 100 mmol/L | 7.3 mg |
| 70 | 7.9 |
| 50 | 5.2 |
| 40 | 5.9 |
| 30 | 8.9 |
| 20 | 5.2 |

Areas of water fill and AgCl precipitation areas were determined after drying using two methods: measurement of area using a computer digitizer with a pen stylus tracer, and calculation of area from diameter measured by a caliper. Precipitation areas were measured at defined times after removal of the sample source. The measured or calculated area of water fill in a partially filled patch was used to calculate the percentage filled for the indicator patch, using the known dimensions of the patch. The percentage filled was then used to convert the actual measured AgCl precipitation area to an extrapolated precipitation area representing an extrapolation to a patch of predefined area that is 100 percent full.

The relationship between sample chloride concentration and extrapolated AgCl precipitation area (based on the extrapolation to 100% water fill) was determined using regression analysis (see FIG. 4). Regression lines were calculated for each time. A linear relationship is also obtained when the ratio of the measured precipitation area to the measured liquid fill area is plotted as a function of chloride concentration; calculation of an extrapolated precipitation area is not necessary.

Results. Phenol red was introduced throughout the test patch in order to allow visualization of the water front as a sample diffuses radially outward from the center hole of the patch. Visualization of the water front permits calculation of the percentage of total patch area actually filled by a sample. Phenol red is a non-halogen pH indicator. As sweat (which normally has a pH of about 7.5) or a test sample moves radially outward from the center hole, a shift in pH occurs, causing the pH indicator (phenol red) to undergo an observable color change that identifies the water front. When collection is stopped and the patch dried, the sample becomes concentrated, causing a further upward pH shift. This shift intensifies the color of the water front providing an easily measurable water fill area.

In order to cause the color change that identifies the water front, the pH of the test sample must be above about pH 7. Although the pH of sweat is generally slightly basic, under unusual conditions a sweat sample with pH of less than 7 is possible. The addition of a small paste pellet of $NaHCO_3$ ensures that the diffusing sample has a pH of at least about 7.5, which is high enough to cause a visible color change in the water fill area.

As the sweat moves radially outward from the center hole, the Cl in the sweat reacts with the $AgCrO_4$ impregnated in the absorbent material, and the resulting insoluble silver salt (AgCl) is precipitated to form a visible area of precipitation.

Correlation coefficients for extrapolated precipitation areas versus chloride concentration were consistently higher than 0.98 (FIG. 4). It was found that when calipers were used to measure the diameters of water area and AgCl precipitation areas, the resulting regression equation and correlation coefficient for the plot of extrapolated precipitation area versus chloride concentration were consistent with that obtained using a computer digitizer with pen stylus to calculate the area Thus, a simple overlay measuring system can, if desired, be used to produce results comparable to that obtainable using computer measuring systems.

The patch was then tested on a human subject. A test patch filled with water front indicator (phenol red) was applied to the skin of a human subject not suffering from cystic fibrosis, and the resulting chloride precipitation area and water fill area (partial fill) were well-defined. Sample weight, determined by subtracting dry patch weight from wet patch weight upon removal of the patch from the skin, was 5.7 mg. The partial fill area and the AgCl precipitation area were measured, and the extrapolated precipitation area (based on 100% fill) was calculated. The chloride concentration of the human sweat sample, based on the regression line calculated from the test samples, was about 19 mmol/L.

Several other pH indicators were tested: aqueous solutions (0.04%) of each of bromocresol green, bromothymol blue, phenol red, and methyl red (Fisher Scientific). All showed some color change. Methyl red showed the least intense color and did not retain the color change. Phenol red (described above) showed the most intense and long-lived color change.

Example 2

Operating Characteristics of the Chloride Test Patch

Materials. The test device described in Example 1, having phenol red dispersed throughout the absorbent layer as described above, was used for the following experiments.

Study (a). The relationship between chloride concentration and precipitation reaction area was determined for completely filled test patches at three chloride concentrations: 20, 50, and 100 mmol/L. The test patches used in this experiment contained an indicator tab. A complete fill was defined by visual observation of the migration of the water front (as shown by the color change) to the edge of the test area, i.e., to the base of the tab on the test patch. At each of these concentrations seven replicate patches were tested, resulting in 21 test patches. Dry patches were first weighed. Patches were then filled by applying 100 μl of sodium chloride (NaCl) solution to a surface composed of a film commercially available under the trade designation "PARAFILM" (Cole-Parmer) to provide a sample source, followed by taping the test patch in place over the solution using a surgical tape commercially available under the trade designation "MICROPORE" (3M Company, St. Paul, Minn.). Upon filling, the patch was removed from the sample source, blotted with tissue paper to remove excess liquid, and weighed. Sample weight was determined by subtracting dry patch weight from wet patch weight.

The area of AgCl precipitation for each patch was measured at seven defined times ranging from zero (i.e., just after a complete fill) to 72 hours after filling. All patches were air dried during the 72 hour period.

Results. Sample weights for the 21 patches ranged from 0.0197 to 0.0227 gm with a mean of 0.0212 gm (about 21 mg) and standard deviation of 0.0009 gm. No significant sample weight difference was noted among the three chloride concentrations.

Mean standard deviations (SD) and regression lines were calculated for the AgCl precipitation area vs. known sample [Cl$^-$] for each of the seven time increments. (Table 2 and 3, FIG. 5). The area of precipitation continued to expand for about 24 hours after removal of the patch from the sample source for the patches exposed to the 50 and 100 mmol/L NaCl concentrations. Precipitation area did not expand appreciably for the patches exposed to the 20 mmol/L solution. The correlation coefficient of area versus chloride concentration was consistent regardless of time of measurement. (Table 3)

TABLE 2

Test Patch AgCl Precipitation Areas as a Function of Time
After Removal from Sample Source
--Complete Patch Fill (about 21 mg)--

| Time | Mean Area (sq mm) 20 mmol/L [Cl$^-$] | SD | Mean Area (sq mm) 50 mmol/L [Cl$^-$] | SD | Mean Area (sq mm) 100 mmol/L [Cl$^-$] | SD |
|---|---|---|---|---|---|---|
| 0 min | 31 | 1.9 | 70 | 4.9 | 115 | 2.9 |
| 30 min | 33 | 1.5 | 72 | 4.9 | 122 | 6.5 |
| 60 min | 34 | 1.9 | 76 | 7.3 | 127 | 4.0 |
| 6 hrs | 35 | 1.5 | 80 | 6.9 | 148 | 4.4 |
| 24 hrs | 35 | 1.3 | 85 | 7.8 | 164 | 6.6 |
| 48 hrs | 36 | 2.1 | 87 | 6.4 | 163 | 9.2 |
| 72 hrs | 36 | 1.4 | 87 | 6.3 | 165 | 6.0 |

TABLE 3

Statistical Analysis of Test Patch AgCl Precipitation Areas vs. [Cl$^-$]
--Complete Patch Fill (approximately 21 mg sample)--

| Time | Regression Equation | Correlation Coefficient |
|---|---|---|
| 0 min | y = 13.367 + 1.0347 x | 0.990 |
| 30 min | y = 13.276 + 1.1010 x | 0.995 |
| 60 min | y = 13.949 + 1.1480 x | 0.992 |
| 6 hrs | y = 7.9286 + 1.4071 x | 0.999 |
| 24 hrs | y = 3.4796 + 1.6092 x | 1.000 |
| 48 hrs | y = 5.7653 + 1.5806 x | 0.999 |
| 72 hrs | y = 4.9286 + 1.6071 x | 0.999 |

Study (b). During clinical use, careful monitoring of the commercially available "CF INDICATOR" patch (Scandipharm, Birmingham, Ala.) is required to avoid accidental overfilling. "CF INDICATOR" patches hold about 20 mg of sample for a "complete fill", but are capable of holding more. The "CF INDICATOR" patch must be observed as it approaches a complete fill, because a completely filled patch cannot be visually distinguished from an overfilled patch. It is quite possible for a technician to glance at a patch and assume that it has been completely filled (and thus use it to make a clinical assessment) without knowing that it has, in fact, been overfilled.

This experiment was conducted to assess the effect of overfilling the test-patch on the size of the AgCl precipitation area, which in turn affects the evaluation of CF risk. An analogous experiment, evaluating the consequences of overfilling, was conducted on the commercially available "CF INDICATOR" patch.

In this study, test patches were excessively filled with about 30 mg of 20, 50, or 100 mmol/L chloride solutions. The time needed to maximally fill the patch (about 30 mg of sample is the maximum it will hold) was determined by weighing the patch periodically during the filling process until no further weight gain was observed. Sample weights were determined to be 29.9 mg for the 20 mmol/L sample, 30.5 for the 50 mmol/L sample, and 30.9 for the 100 mmol/L sample. The area of precipitation for each patch was measured at defined times from zero (i.e., the time when the sample source was removed) to 72 hours. All patches were dried over CaSO$_4$ during the 72 hour period.

Results. The addition of about 50% more sodium chloride solution to the patch caused an increase in the observed precipitation area of about 30 to 40%. (compare Table 4 to Table 2). Similar results were observed for the commercially "CF INDICATOR" patch. From these results, it can be reasonably concluded that overfilling the commercially "CF INDICATOR" patch in a clinical setting can lead to false positive diagnosis of CF.

TABLE 4

Test Patch AgCl Precipitation Areas as a Function of Time
--Excess Patch Fill (approximately 30 mg sample)--

| Time | Area (sq mm) 20 mmol/L [CL$^-$] | Area (sq mm) 50 mmol/L [CL$^-$] | Area (sq mm) 100 mmol/L [CL$^-$] |
|---|---|---|---|
| 0 min | 43 | 92 | 141 |
| 30 min | 43 | 98 | 155 |
| 60 min | 44 | 97 | 156 |
| 6 hrs | 45 | 99 | 164 |
| 24 hrs | 45 | 96 | 164 |
| 48 hrs | 45 | 104 | 178 |
| 72 hrs | 47 | 101 | 179 |

Study (c). It had been previously noted that the area of AgCl precipitation continues to expand for a time even after the test patch is removed from the sample source. Accelerated drying was therefore performed to determine whether continued migration of the precipitation reaction area could be arrested after removal of the sample source. Patches were filled to a "complete fill" (about 21 mg) as in study (a), with 20, 50, and 100 mmol/L sodium chloride solutions (7 test patches per solution), and sample weights for the 21 patches were determined immediately after complete filling. The patches were then placed in small zip-lock bags containing CaSO$_4$ drying compound. The amount of water removed was determined by weighing every 10 minutes during the first 30 minutes following removal of the sample source, and periodically over the next 96 hours. The precipitation area was also measured at each of these time points to determine whether accelerated drying was effective in stopping the migration of the precipitation area.

Results. The mean precipitation areas and standard deviations for test patches as a function of drying time after removal of the filled patch from the sample source are shown in Table 5.

TABLE 5

Test Patch AgCl Precipitation Areas as a Function of Time After Removal from Sample Source and Accelerated Drying --Complete Patch Fill (about 21 mg)--

| Time | Mean Area (sq mm) 20 mmol/L [Cl⁻] | SD | Mean Area (sq mm) 50 mmol/L [Cl⁻] | SD | Mean Area (sq mm) 100 mmol/L [Cl⁻] | SD |
|---|---|---|---|---|---|---|
| 0 min | 29 | 2.4 | 67 | 3.0 | 111 | 4.0 |
| 30 min | 30 | 1.6 | 69 | 3.8 | 116 | 4.0 |
| 48 hrs | 29 | 1.9 | 68 | 3.0 | 120 | 5.4 |

The regression lines and equations for precipitation area versus chloride concentration of all measurements from zero to 48 hours are presented in FIG. 6 and Table 6.

TABLE 6

Statistical Analysis of Test Patch AgCl Precipitation Areas vs. [Cl⁻] Accelerated Drying after Removal of Sample Source --Complete Patch Fill (approximately 21 mg sample)--

| Time | Regression Equation | Correlation Coefficient |
|---|---|---|
| 0 min | y = 11.755 + 1.0102 x | 0.990 |
| 30 min | y = 11.531 + 1.0612 x | 0.992 |
| 48 hrs | y = 8.4388 + 1.1276 x | 0.996 |

Example 3

Quality Control of Test Patches

Figure 7:
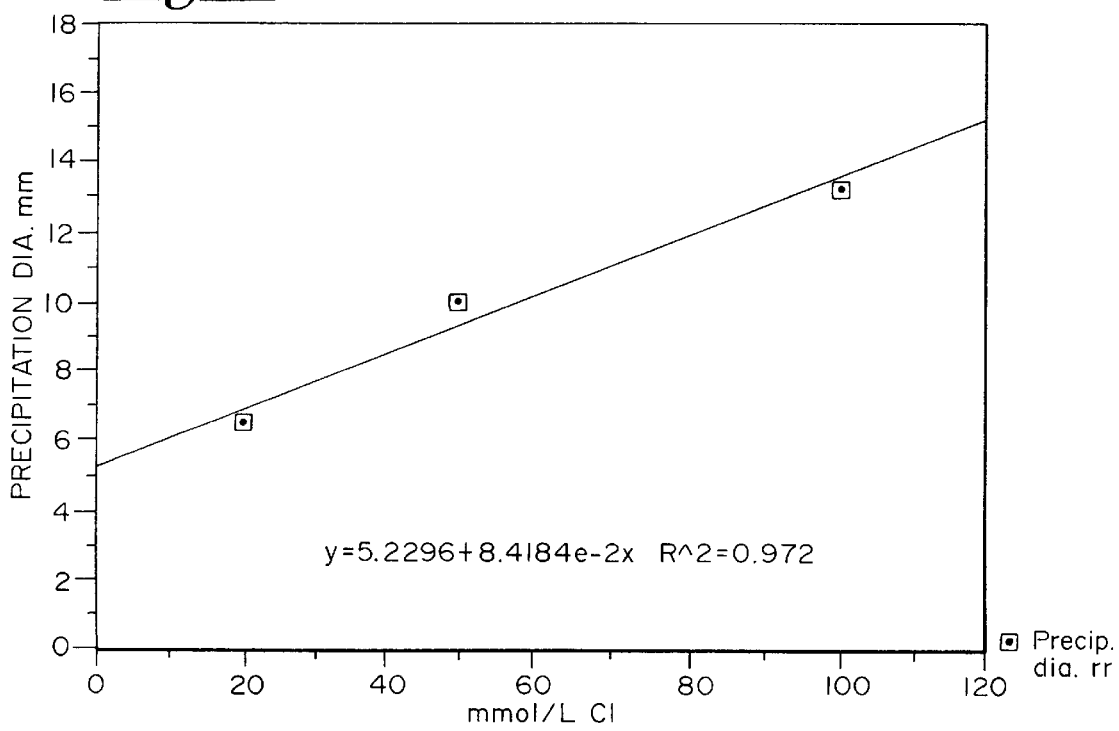
FIG. 7 is a graph depicting a regression line fit to a plot of precipitation area diameters versus chloride concentration for completely filled test patches dried over $CaSO_4$.

Mean diameters of the AgCl precipitation areas for a complete fill of 21 test patches were determined using three standard chloride solutions 20, 50, and 100 mmol/L. A regression line with correlation coefficient was calculated. (FIG. 7). Using that regression line, the expected diameter of each concentration was calculated. Each of the 21 measured mean diameters was subtracted from the expected value. A standard deviation was then calculated on these differences. The standard deviation is 0.27 mm. If a solution of 45 mmol/L Cl⁻ is used, the expected diameter is 8.98 mm. Plus or minus two standard deviations from 8.98 mm is 8.44 mm to 9.52 mm. This translates into a range of 39 mmol/L to 51 mmol/L Cl⁻ (coefficient of variation=6.7%). Thus, if a 45 mmol/L Cl⁻ solution is used as a quality control standard, it should fall within the above range on a control test patch. Ninety-five percent of all tests would be expected to fall within that range.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A device of substantially flat construction for application to the skin of a patient, collection of a test sample of sweat, and quantitative determination of the chloride concentration in the test sample of sweat, comprising:
   a top transparent liquid-impermeable layer;
   a bottom liquid-impermeable layer for contacting the skin comprising a centrally located inlet and a plurality of channels extending radially from the inlet for collecting the sweat and directing the sweat toward the inlet; and
   a middle layer between the top and bottom layers comprising an absorbent material having substantially uniformly dispersed throughout at least a portion thereof (i) a liquid-detecting agent capable of detectably delimiting the liquid front formed as the liquid portion of the test sample migrates radially outwardly from the inlet through the substantially flat absorbent material, and (ii) a partitioning agent comprising a species capable of complexing with chloride ions present in the test sample to form a detectable precipitate disposed radially inwardly of said liquid front.

2. The device of claim 1 wherein the partitioning agent comprises silver chromate.

3. The device of claim 1 wherein the liquid-detecting substance comprises a pH indicator.

4. The device of claim 1 wherein the pH indicator comprises phenol red.

5. The device of claim 1 wherein the alkaline substance comprises sodium bicarbonate.

6. The device of claim 1 wherein the bodily fluid is sweat obtained from a patient suspected of being afflicted with cystic fibrosis.

7. A device for quantitatively determining the concentration of a chloride ion containing analyte in a liquid sample comprising:
   a first liquid-impermeable layer;
   a second liquid-impermeable layer comprising an inlet for the introduction of the liquid sample; and
   a third layer between the first and second liquid-impermeable layers comprising an absorbent material comprising (i) a liquid-detecting agent capable of detectably delimiting the liquid front formed as the liquid migrates radially outwardly from the inlet through the absorbent material, and (ii) a partitioning agent capable of detectably removing the chloride ions in the analyte from the liquid sample through complexing with chloride ions present in the liquid of said sample.

8. The device of claim 7, wherein at least one of the first and second liquid impermeable layers is transparent.

9. The device of claim 7, wherein the partitioning agent is distributed substantially uniformly throughout at least a portion of the absorbent material.

10. The device of claim 7, wherein the partitioning agent comprises a species capable of forming a detectable complex comprising the analyte.

11. The device of claim 10, wherein the detectable complex comprises a precipitate comprising the analyte.

12. The device of claim 7, wherein the partitioning agent is bound to the absorbent material.

13. The device of claim 12, wherein the bound partitioning agent comprises a species capable of binding the analyte to form a detectable complex bound to the absorbent material.

14. The device of claim 7, wherein the analyte is a chloride ion.

15. The device of claim 14, wherein the partitioning agent comprises silver chromate.

16. The device of claim 1, wherein the inlet comprises an alkaline material capable of ensuring that the pH of the liquid sample entering the device is at least about pH 7.0.

17. A device for quantitatively determining the concentration of chloride ion present in an analyte in a liquid sample comprising:

a first liquid-impermeable layer;

a second liquid-impermeable layer comprising an inlet for the introduction of the liquid sample; and a third layer between the first and second liquid-impermeable layers comprising an absorbent material comprising (i) a measurable fill area delimited by a detectable water front formed by a liquid sample introduced into the device through the inlet for radial outward migration therefrom; and (ii) a measurable detection area comprising a component capable of species specific complexing with chloride ions for forming an immobilized or insoluble detectable complex comprising the analyte.

18. A method for preparing a device for quantitatively determining the concentration of chloride ions present in an analyte in a liquid sample comprising:

(a) distributing throughout at least a portion of an absorbent material each of:
  (i) a liquid-detecting agent, and
  (ii) a partitioning agent capable of detectably removing chloride present in the analyte from the liquid sample; and (b) positioning the absorbent material between a first liquid-impermeable layer and a second liquid-impermeable layer comprising an inlet for introduction of the liquid sample, wherein the liquid-detecting substance is capable of detectably delimiting the liquid front formed as the liquid containing chloride ion migrates from the inlet through the absorbent material.

19. The method of claim 18, wherein the partitioning agent comprises silver chromate.

20. The method of claim 19, wherein the silver chromate is formed in situ in the absorbent material.

21. The method of claim 17, further comprising (c) inserting into the inlet a paste or plug comprising an alkaline substance capable of ensuring that the pH of a liquid sample entering the device is at least about pH 7.0.

22. A method for determining the concentration of an analyte in a liquid sample comprising:

providing a device comprising a first liquid-impermeable layer, a second liquid-impermeable layer comprising an inlet, and a third layer between the first and second liquid-impermeable layers, said third layer comprising an absorbent material comprising each of a liquid-detecting agent and a partitioning agent;

introducing an amount of the liquid sample into the inlet of the device such that the liquid diffuses through the absorbent material so as to contact both the liquid-detecting agent and the partitioning agent, wherein contact of the liquid with the liquid-detecting agent allows detection of a water front delimiting a fill area of the absorbent material, and wherein contact of the liquid with the partitioning agent causes formation of a detectable complex comprising the analyte thereby effecting removal of the analyte from the liquid, the area of formation of said detectable complex constituting a detection area of the absorbent material;

obtaining a measurement of the fill area;

obtaining a measurement of the detection area; and evaluating the fill area measurement and the detection area measurement to determine the concentration of the analyte in the liquid sample.

23. The method of claim 22, wherein the detectable complex comprises a precipitate comprising the analyte, and wherein the detection area is a precipitation area.

24. The method of claim 22, wherein the evaluation step comprises evaluating the fill area measurement and the detection area measurement in view of an empirically derived standard curve to determine the concentration of the analyte in the liquid sample.

25. The method of claim 22, wherein a computer is used to obtain the detection area measurement and the fill area measurement.

26. The method of claim 22, wherein a computer is used to evaluate the detection area measurement and the fill area measurement.

27. A method for performing a diagnostic test for cystic fibrosis comprising:

inducing the production of sweat on the skin of a patient;

applying the bottom layer of the device of claim 1 to the skin of the patient such that the sweat enters the device through the inlet and diffuses through a portion of the absorbent material to yield a precipitation area comprising a detectable precipitate comprising the chloride ions, and a fill area detectably delimited by the liquid front;

obtaining a measurement of the precipitation area;

obtaining a measurement of the fill area; and evaluating the precipitation area measurement and the fill area measurement to determine the concentration of chloride ions in the sweat, wherein the concentration of chloride ions in the sweat is used to diagnose the presence or absence of cystic fibrosis.

28. A diagnostic kit for screening for cystic fibrosis comprising at least one of the device of claim 1 and instructions for use of the device.

29. The diagnostic kit of claim 28 further comprising a known amount of a chloride salt, and at least one device of claim 1 to serve as a quality control.

30. The diagnostic kit of claim 28 further comprising an aqueous solution comprising a known concentration of a chloride salt, and at least one device of claim 1 to serve as a quality control.

31. The diagnostic kit of claim 30 wherein the chloride salt is sodium chloride.

32. The diagnostic kit of claim 28, further comprising a standard curve, a mathematical equation, or both, for use in determining chloride concentration in a test sample using a measurement of a test sample precipitation area, wherein the test sample precipitation area comprises a precipitate comprising chloride and the substance capable of visibly reacting with chloride.

33. A device of substantially flat construction for application to the skin of a patient, collection of a test sample of sweat, and determination of the chloride concentration in the test sample of sweat, comprising:

a top transparent liquid-impermeable layer;

a bottom liquid-impermeable layer for contacting the skin comprising a centrally located inlet and a plurality of channels extending radially from the inlet for collecting the sweat and directing the sweat toward the inlet;

a middle layer between the top and bottom layers comprising an absorbent material having substantially uniformly dispersed throughout at least a portion thereof (i) a liquid-detecting agent capable of detectably delimiting the liquid front formed as the test sample migrates from the inlet through the substantially flat absorbent material, and (ii) a partitioning agent comprising a species capable of complexing with chloride ions to form a detectable precipitate; and wherein said inlet comprises an alkaline substance capable of ensuring that the pH of the sweat entering the device is at least about pH 7.0.

34. A device for determining the concentration of an analyte in a liquid sample comprising:

a first liquid-impermeable layer;

a second liquid-impermeable layer comprising an inlet for the introduction of the liquid sample;

a third layer between the first and second liquid-impermeable layers comprising an absorbent material comprising (i) a liquid-detecting agent capable of detectably delimiting the liquid front formed as the liquid migrates from the inlet through the absorbent material, and (ii) a partitioning agent capable of detectably removing the analyte from the liquid sample; and the liquid-detecting agent comprises a pH indicator.

35. A method for preparing a device for determining the concentration of an analyte in a liquid sample comprising:

(a) distributing throughout at least a portion of an absorbent material each of
 (i) a liquid-detecting agent, and
 (ii) a partitioning agent capable of detectably removing the analyte from the liquid sample;

(b) positioning the absorbent material between a first liquid-impermeable layer and a second liquid-impermeable layer comprising an inlet for introduction of the liquid sample, wherein the liquid-detecting substance is capable of detectably delimiting the liquid front formed as the liquid migrates from the inlet through the absorbent material; and (c) the liquid-detecting substance comprises a pH indicator.

* * * * *